(12) United States Patent
Vincent

(10) Patent No.: US 8,540,858 B2
(45) Date of Patent: Sep. 24, 2013

(54) INTERDIGITATED MICROELECTRODE AND A PROCESS FOR PRODUCING THE INTERDIGITATED MICROELECTRODE

(75) Inventor: David Robert Vincent, Ferndown (GB)

(73) Assignee: Intellitect Water Limited, Dorset (GB)

( * ) Notice: Subject to any disclaimer, the term of this patent is extended or adjusted under 35 U.S.C. 154(b) by 892 days.

(21) Appl. No.: 12/087,940

(22) PCT Filed: Jan. 25, 2007

(86) PCT No.: PCT/GB2007/000259
§ 371 (c)(1),
(2), (4) Date: Jul. 17, 2008

(87) PCT Pub. No.: WO2007/085838
PCT Pub. Date: Aug. 2, 2007

(65) Prior Publication Data
US 2008/0314744 A1    Dec. 25, 2008

(30) Foreign Application Priority Data
Jan. 27, 2006  (GB) .................................. 0601703.2

(51) Int. Cl.
*C25B 11/02*   (2006.01)
*C25B 11/04*   (2006.01)

(52) U.S. Cl.
USPC ..................................... 204/290.14; 204/289

(58) Field of Classification Search
USPC ................... 204/280, 286.1, 288, 288.2, 289, 204/290.01, 290.14; 101/129
See application file for complete search history.

(56) References Cited

U.S. PATENT DOCUMENTS

| 5,425,869 A | 6/1995 | Noding et al. |
| 5,670,031 A * | 9/1997 | Hintsche et al. ........... 205/777.5 |
| 6,270,651 B1 | 8/2001 | Essalik et al. |
| 2006/0194331 A1 * | 8/2006 | Pamula et al. ................ 436/150 |
| 2006/0211123 A1 * | 9/2006 | Ker et al. ...................... 436/113 |

FOREIGN PATENT DOCUMENTS

EP    0593096 A    4/1994

* cited by examiner

Primary Examiner — J. Christopher Ball
(74) Attorney, Agent, or Firm — Iandiorio Teska & Coleman LLP

(57) ABSTRACT

An interdigitated microelectrode (2) comprising a substrate (4), a first layer (6) of a first metal on the substrate (4), and a second layer (8) of a second metal on the substrate (4), the first layer (6) comprising a plurality of line microelectrodes (10) which are connected at a first end (12) and are not connected at a second end (14), the second layer (8) comprising a plurality of line microelectrodes (16) which are connected at a first end (18) and are not connected at a second end (20), the line microelectrodes (10) of the first layer (6) and the line microelectrodes (16) of the second layer (8) being such that they extend into each other but do not touch each other thereby to form an interdigititated microelectrode array (22), and the first metal being different from the second metal. A process for producing the interdigitated microelectrode (2) is also disclosed.

6 Claims, 6 Drawing Sheets

INTERDIGITATED MICROELECTRODE AND A PROCESS FOR PRODUCING THE INTERDIGITATED MICROELECTRODE

This invention relates to an interdigitated microelectrode, and to a process for producing the interdigitated microelectrode. The interdigitated microelectrode may be used as an electrochemical sensor, for example in the form of a water sensing device for sensing properties in water.

Interdigitated microelectrodes for use as electrochemical sensors are well known. The electrochemical sensors are used in the study of redox cycling electrochemical reactions, and for measuring chemical species where a signal at a second electrode is improved by the presence of species generated at the first electrode. One such example of the measurement of chemical species is in the measurement of dissolved oxygen, where the potential required to detect the oxygen is reduced by the presence of protons which are generated at a first electrode and which lower the pH. Another example of the measurement of chemical species is the measurement of chlorine in water. In the majority of the known electrochemical sensors, the microelectrodes are manufactured on a silicon base, using expensive microelectronic processes. Due to the complexity of these microelectronic processes and their attendant costs, the first and the second microelectrodes are made from the same metal. This means that if one of the desired reactions must take place on an electrode of a particular type, the effectiveness of the other electrode may be compromised.

It is an aim of the present invention to obviate or reduce the above mentioned problems.

Accordingly, the present invention provides an interdigitated microelectrode comprising a substrate, a first layer of a first metal on the substrate, and a second layer of a second metal on the substrate, and the interdigitated microelectrode being such that the first layer comprises a plurality of line microelectrodes which are connected at a first end and are not connected at a second end, the second layer comprises a plurality of line microelectrodes which are connected at a first end and are not connected at a second end, the line microelectrodes of the first layer and the line microelectrodes of the second layer extend into each other but do not touch each other thereby to form an interdigitated microelectrode array, the first layer of the first metal is a thick film printed first layer, the second layer of the second metal is a thick film printed second layer, the line width of the line microelectrodes of the second layer is such that the line width has been reduced after deposition of the second layer on the substrate, the line width has been reduced by thin film photolithography and etching, the line width has been reduced to less than 25 microns wide, the first metal is different from the second metal, and the second metal is gold.

The present invention also provides a process for producing an interdigitated microelectrode, which process comprises providing a substrate, providing a first layer of a first metal on the substrate, and providing a second layer of a second metal on the substrate, and the process being such that the first layer comprises a plurality of line microelectrodes which are connected at a first end and are not connected at a second end, the second layer comprises a plurality of line microelectrodes which are connected at a first end and are not connected at a second end, the line microelectrodes of the first layer and the line microelectrodes of the second layer extend into each other but do not touch each other thereby to form an interdigitated microelectrode array, the first layer of the first metal is a thick film printed first layer, the second layer of the second metal is a thick film printed second layer, the line width of the line microelectrodes of the second layer is such that the line width has been reduced after deposition of the second layer on the substrate, the line width has been reduced by photolithography and etching, the line width has been reduced to less than 25 microns wide, the first metal is different from the second metal, and the second metal is gold.

The interdigitated microelectrode of the present invention is such that it is able to be produced by a process which is less costly and less complex than known manufacturing processes. This enables the first and the second metals to be different from each other so that the problem associated with using the same metal for the first and the second electrodes is overcome.

The interdigitated microelectrode and the process of the present invention may include the provision of registration means for use in ensuring that the line microelectrodes of the first layer and the line microelectrodes of the second layer do not touch each other. The line microelectrodes of the second layer can be provided such that they are correctly aligned. The registration means may be first and second formations provided on the substrate. Preferably, the registration means, for example the first and the second formations, are provided on the substrate at the time of providing the first layer of the first metal.

The interdigitated microelectrode and the process of the present invention may include providing first electrical connection means for the first layer of the first metal. The first electrical connection means may be a through hole. The through hole may be a plated through hole. Other types of first electrical connection means may be employed.

The interdigitated microelectrodes and the process of the present invention may include providing second electrical connection means for the second layer of the second metal. The second electrical connection means may be a through hole. The through hole may be a plated through hole. Other types of second electrical connection means may be employed.

The first layer of the first metal may be provided by silk screen printing.

The second layer of the second metal may be provided by silk screen printing.

The interdigitated microelectrode and the process of the present invention may include providing a sealing layer which seals parts of the interdigitated microelectrode but which does not seal the interdigitated microelectrode array. The sealing layer may be a dielectric sealing layer. Other types of sealing layer may be employed.

Preferably, the first metal is platinum. Other first metals may be employed. Preferably the substrate is a ceramic substrate, for example a silicon substrate or sintered alumina. Other substrates may be employed. The substrate may be glazed or unglazed.

The present invention also extends to an interdigitated microelectrode when produced by the process of the invention.

The present invention also extends to an electrochemical sensor comprising the interdigitated microelectrode. The electrochemical sensor is preferably in the form of a water sensing device for sensing properties in water. The water sensing device may be used to sense properties in water on its own, in water in aqueous solutions, in water in the air, or in water in oil.

Embodiments of the invention will now be described solely by way of example and with reference to the accompanying drawings in which.

Figure 1:
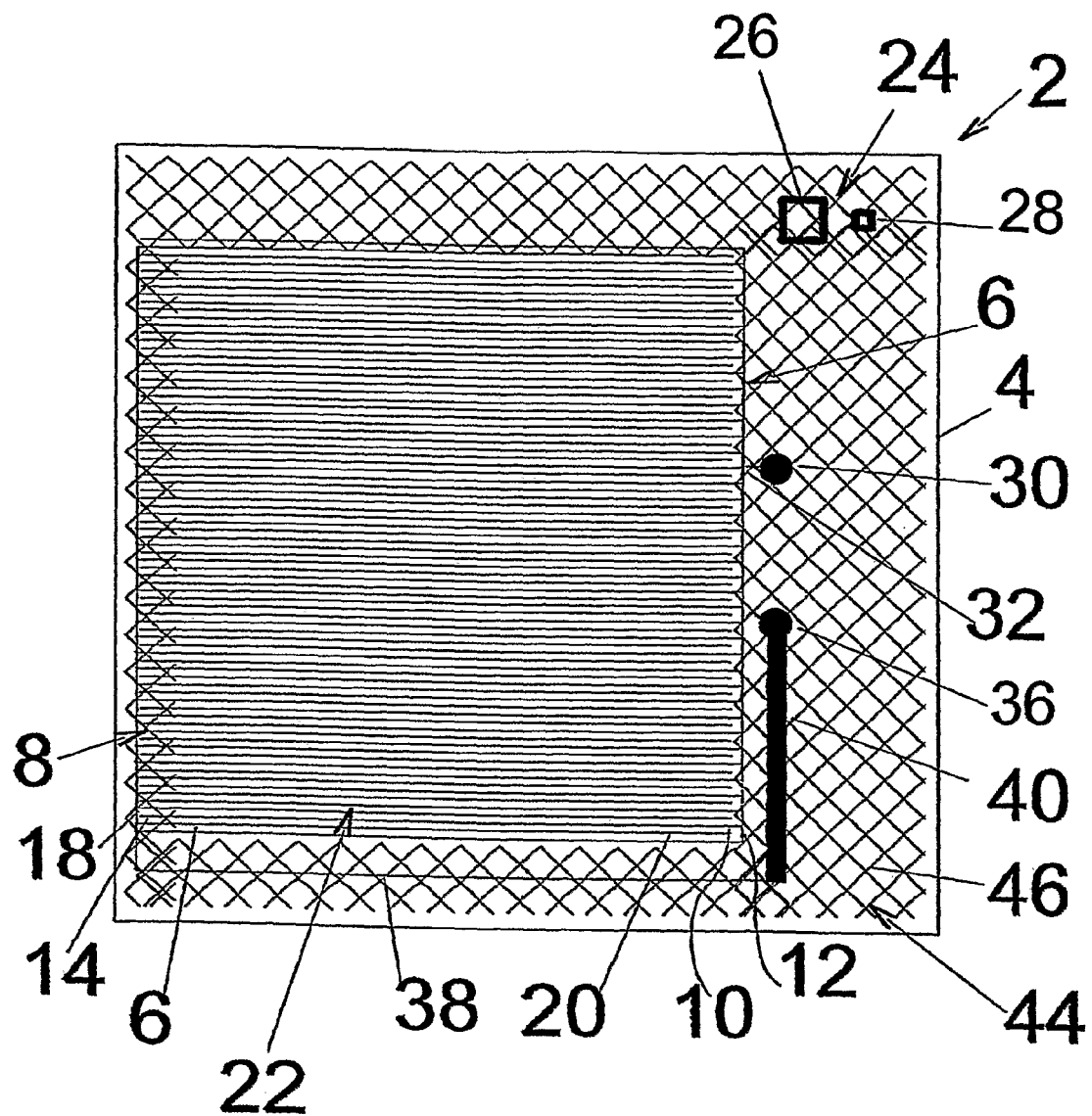
FIG. 1 shows an interdigitated microelectrode.

Referring to the drawings, there is shown an interdigitated microelectrode 2 comprising a substrate 4. A first layer 6 of a first metal is on the substrate 4. A second layer 8 of a second metal is also provided on the substrate 4. The first layer 6 comprises a plurality of line microelectrodes 10 which are connected at a first end 12 and which are not connected at a second end 14. The second layer 8 comprises a plurality of line microelectrodes 16 which are connected at a first end 18 and which are not connected at a second end 20.

As can be seen from FIG. 1, the line microelectrodes 10 of the first layer 6 and the line microelectrodes 16 of the second layer 8 extend into each other. They do not touch each other. They form an interdigitated microelectrode array 22. The first metal of the first layer 6 is different from the second metal of the second layer 8.

The interdigitated microelectrode 2 includes registration means 24 for ensuring that the line microelectrodes 10 of the first layer 6 and the line microelectrodes 16 of the second layer 8 do not touch each other. The registration means 24 comprises a first square formation 26 and a second and smaller square formation 28.

The interdigitated microelectrode 2 includes first electrical connection means 30 for the first layer 6 of the first metal. The first end 12 of the first layer 6 is connected by line 32 to the first electrical connection means 30 which is in the form of a through plated hole plated with the first metal. Similarly, the interdigitated microelectrode 2 includes second electrical connection means 36 for the second layer 8 of the second metal. The second electrical connection means 36 is a through plated hole which is connected to the second layer 8 by a line 38 and a strip 40. The line 38 and the strip 40 form part of the second layer 8. The first layer 6 of the first metal and the second layer 8 of the second metal are thick film printed layers, which are provided by silk screen printing.

Figure 6:
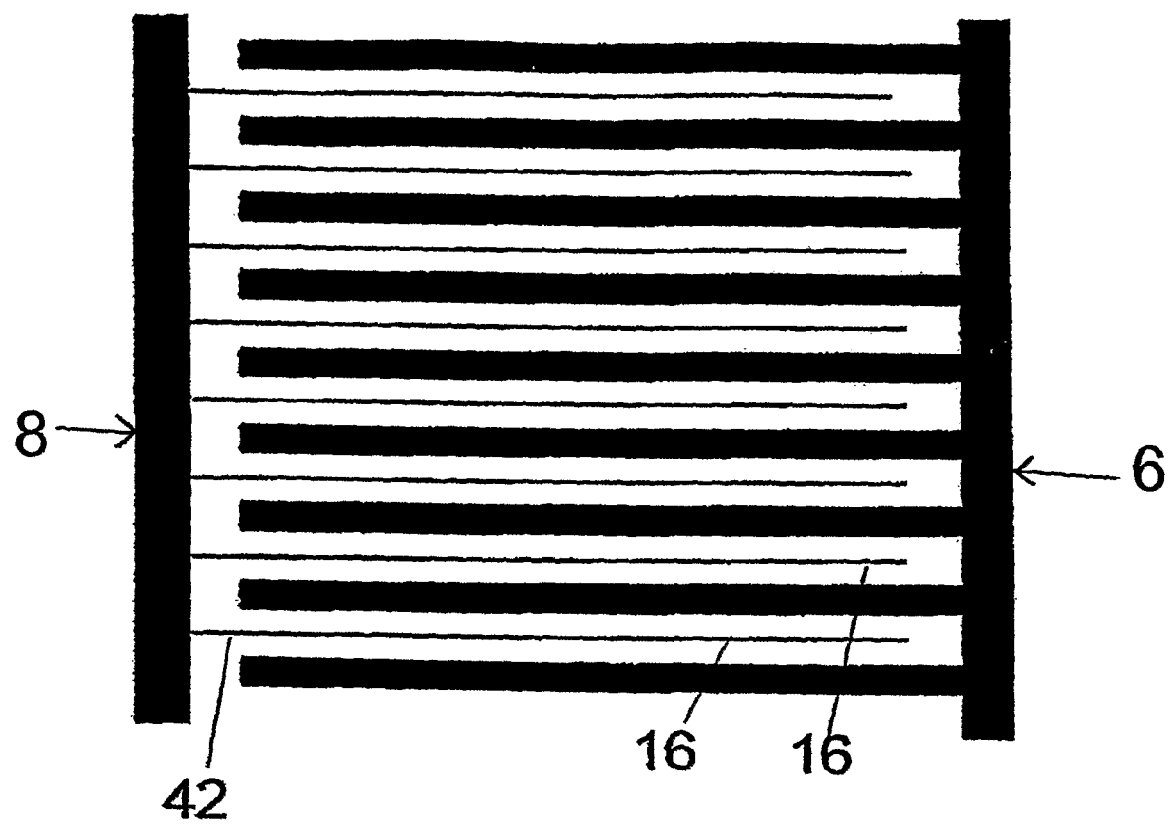
FIG. 6 shows an enlarged view how the line width of line microelectrodes in the second layer has been reduced.

As shown in FIG. 6, the line width 42 of the line microelectrodes 16 is reduced after deposition of the second layer 8 on the substrate 4. The line width 42 is reduced to the required width size by photolithography and etching. As shown in FIG. 6, the line width is less than 25 microns.

As shown in FIG. 1, the interdigitated microelectrode 2 is provided with a sealing layer 44 which seals outer peripheral parts 46 of the interdigitated microelectrode 2, but which does not seal the interdigitated microelectrode array 22.

The interdigitated microelectrode 2 is such that the sealing layer 44 is a dielectric sealing layer, the first metal is platinum, the second metal is gold, and the substrate is a ceramic substrate in the form of silicon.

The process of producing the interdigitated microelectrode 2 shown in FIG. 1 can be appreciated from FIGS. 2-6 which show sequentially various stages in the formation of the interdigitated microelectrode 2. A preferred manufacturing process is as follows. This preferred manufacturing process may be summarised as comprising the following steps.

Figure 2:
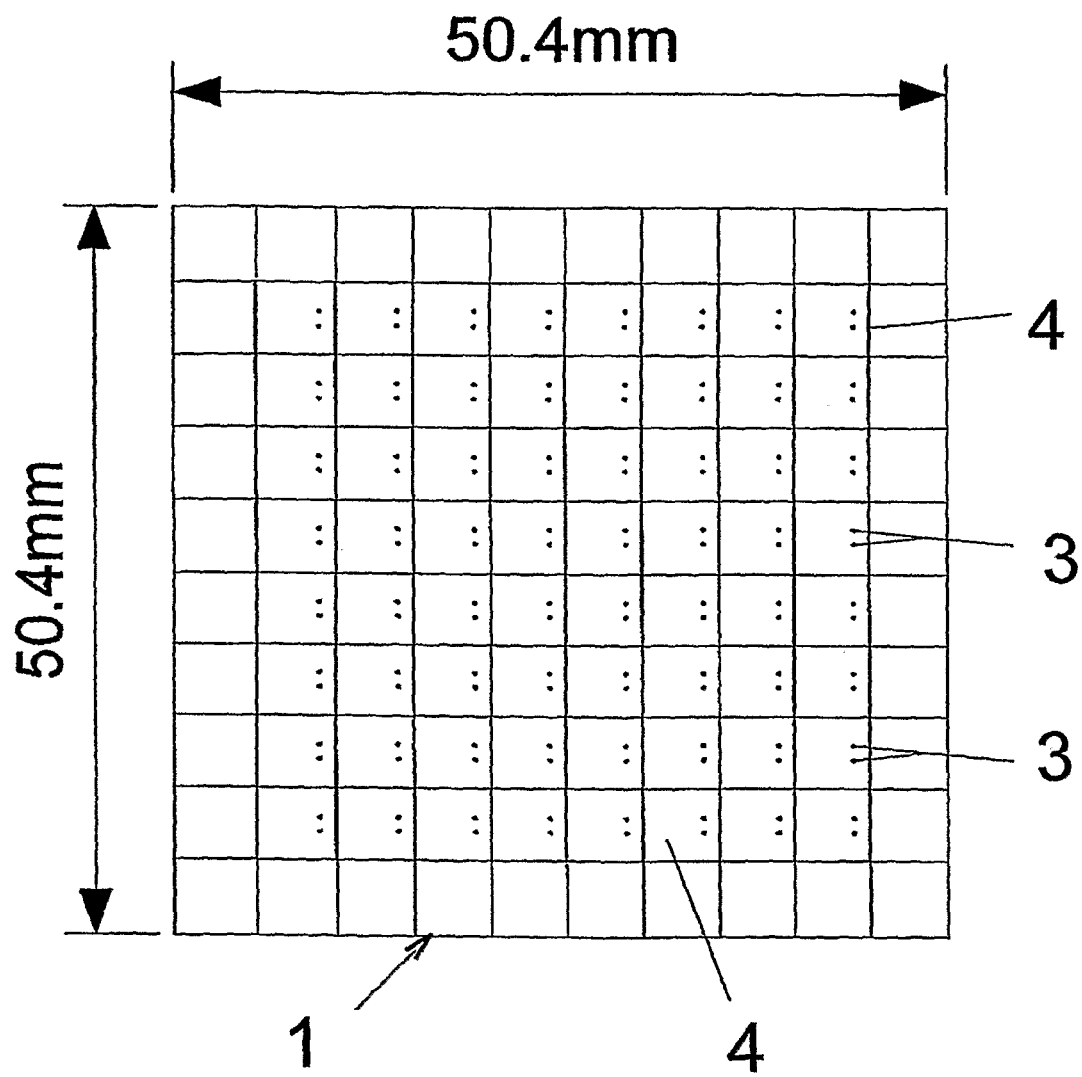
FIG. 2 shows how a substrate sheet is able to be marked to form a plurality of different pieces of substrate which can then be separated into individual pieces of substrate.
Figure 3:
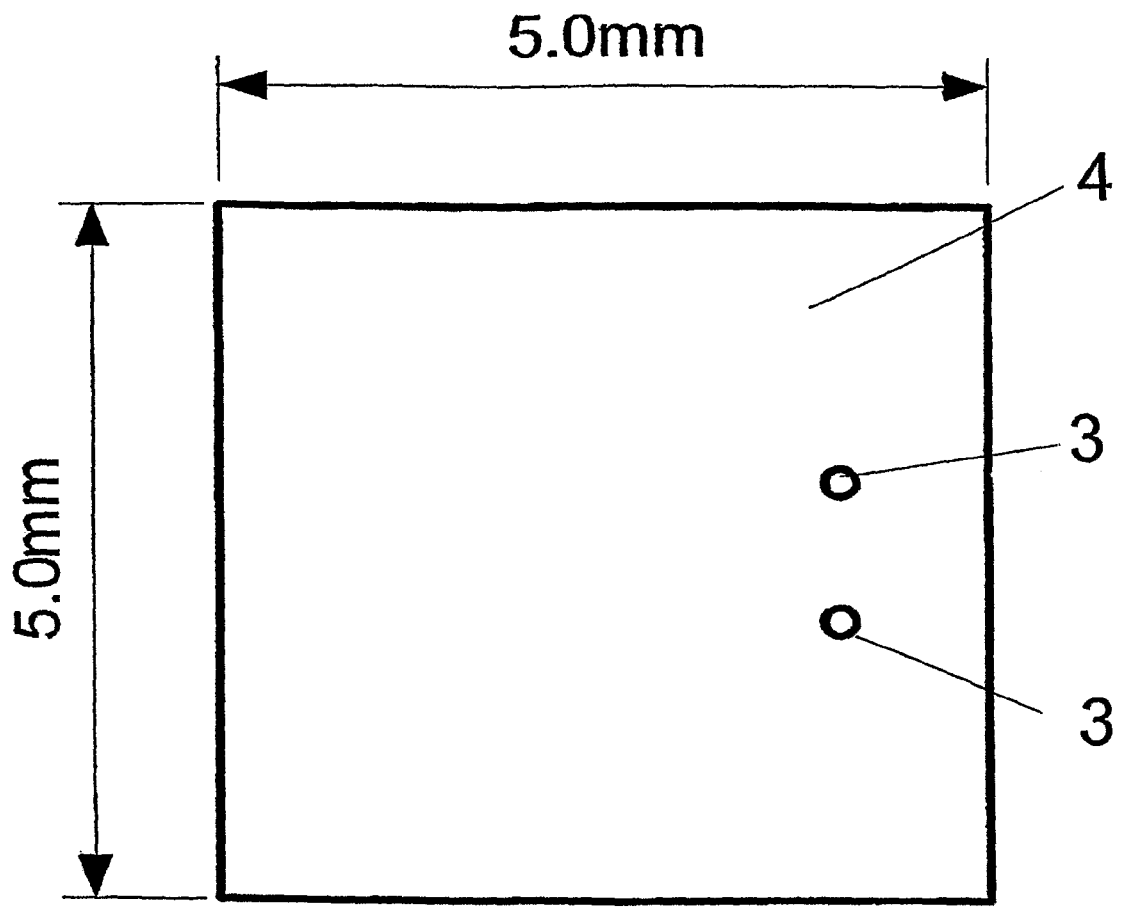
FIG. 3 shows in enlarged form one of the pieces of substrate obtained from FIG. 2, the piece of substrate shown in FIG. 2 being the substrate shown in FIG. 1.
Figure 4:
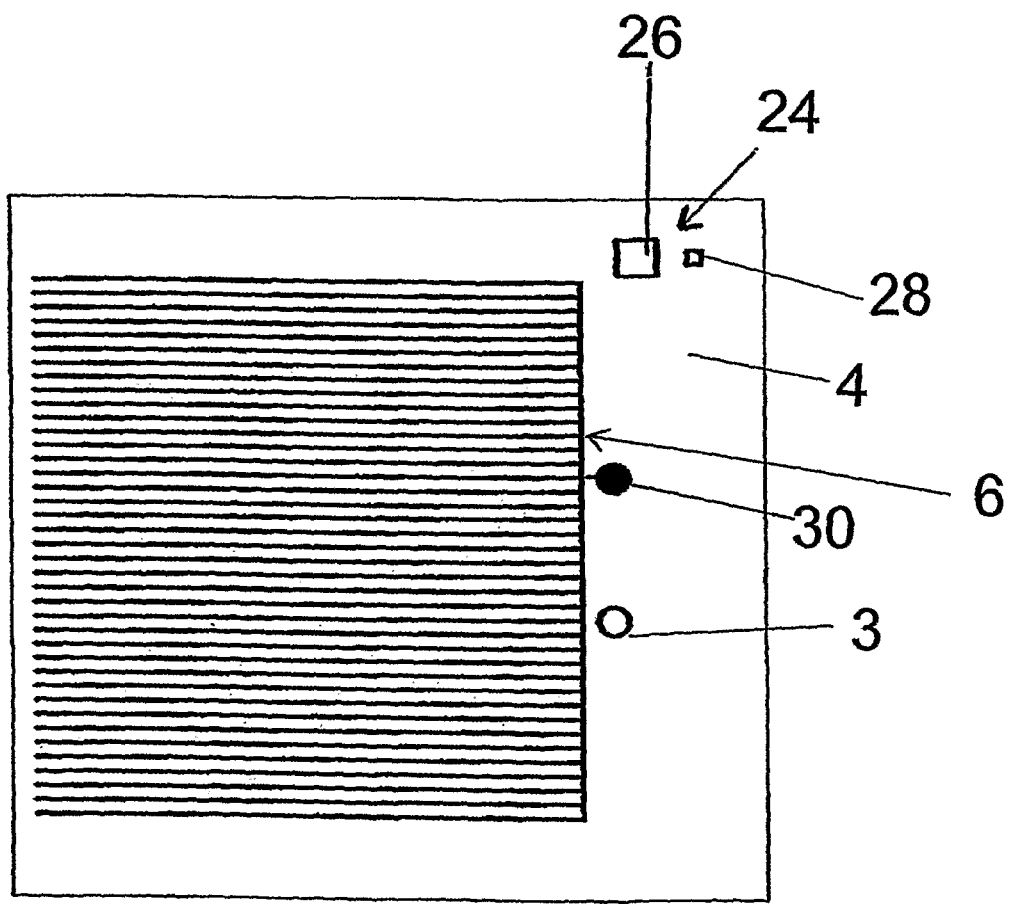
FIG. 4 shows the substrate of FIG. 3 provided with a first layer of a first metal, and with registration means.
Figure 5:
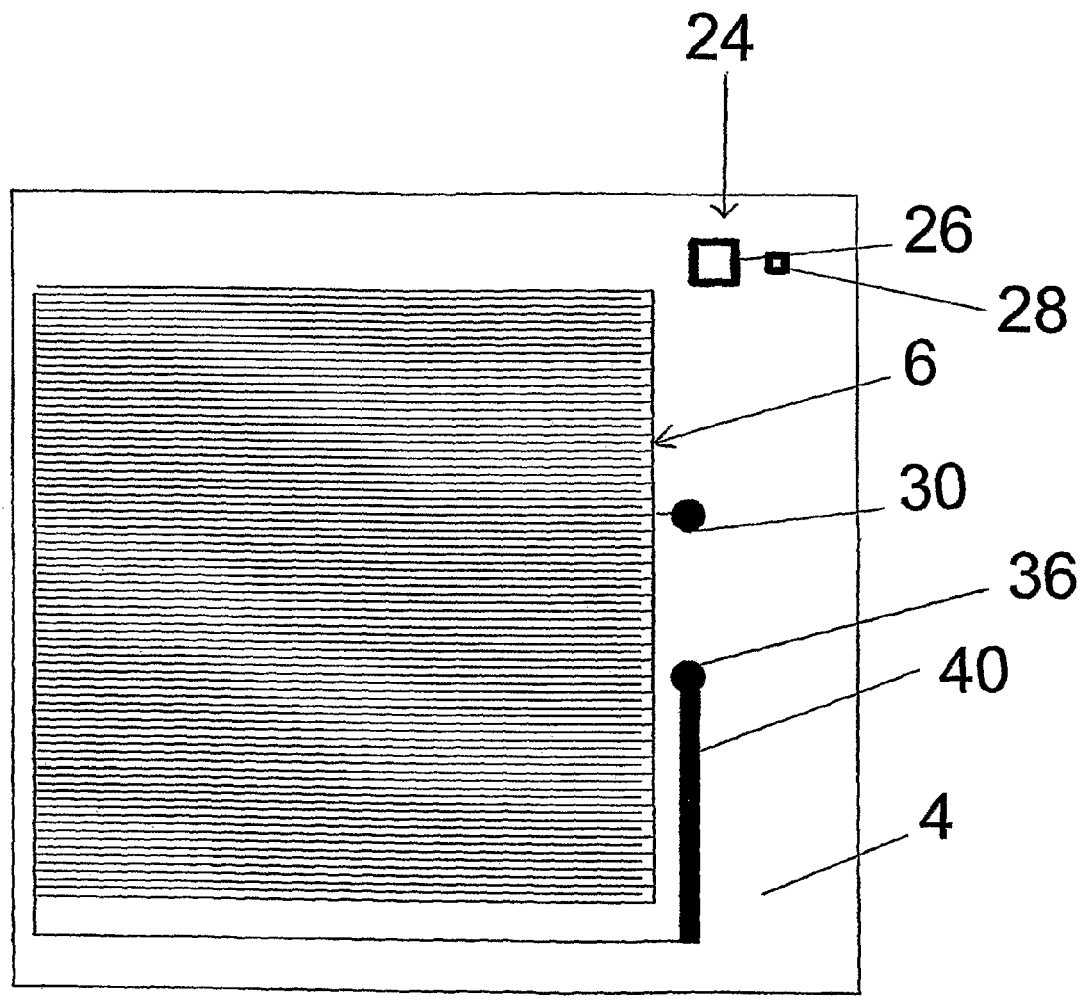
FIG. 5 shows the product of FIG. 4 additionally provided with a second layer of a second metal.

1. Process a ceramic substrate 1, forming holes 3 and laser scribing individual substrate shapes as shown in FIG. 2, to form individual substrates 4 as shown in FIG. 3.
2. Print the first layer 6 of the first metal as shown in FIG. 4, lining up with the registration means 24.
3. Print the second layer 8 of the second metal as shown in FIG. 5, lining up with the first layer 6 of the first metal.
4. Etch the second layer 8 of the second metal using photolithography to achieve required definition and line width as shown in FIG. 6.
5. If necessary, through plate the connection holes forming the registration means 24.
6. Print the sealing layer 44 of the hermetically sealing dielectric material in order to waterproof the interdigitated microelectrode 2 where necessary, so that only the thin parts of the interdigitated microelectrode array 22 are exposed.

In the process of the present invention, the first layer 6 may be of 5 mm×5 mm in size, and it may be printed on a substrate 4 which has a thickness of 0.625 mm. The printing may be thick film printing using silk screen printing of a platinum resonate ink. The platinum resonate ink is typically dried and baked, and may be reprinted for increased electrode track thickness. The first and the second square formations 26, 28 are of different sizes as mentioned above. If desired, only one of the formations may be employed, then in this case it may be of 0.1-3 mm across. The line microelectrodes 10 of the first layer 6 may be of line width limited by the capabilities of the printing apparatus providing the first layer 6. The line width may be from 50-250 µm and 2-5 mm long. Other dimensions may of course be employed. The through plated hole connection (or other appropriate electrical connection means) is able to be used for making an electrical connection to the rear side of the interdigitated microelectrode 2 as shown in FIG. 1.

The second layer 8 is printed as a gold layer, which is aligned with the first layer 6 using the registration means 24. The gold is in the form of a gold ink that is designed to be etched and re-baked at high temperatures, whilst maintaining good adhesion to the substrate 4. The thick film deposition of the first and the second layers 6, 8 respectively is a low cost method of providing the first and the second layers 6, 8 on the substrate 4. The gold layer 8 may be used for chlorine detection in water. The gold layer 8 is processed using photolithography to reduce the line width as illustrated in FIG. 6. This reduction of the line width is effected using a thin film process. The registration means 24 is able to be used in order to minimise alignment errors, which is advantageous if the thin film process to reduce the line width takes place at a separate site. Thin film photolithography is a more precise process than thick film screen printing, and the more precise process may be required in order to obtain the required line width.

The final processing of the interdigitated microelectrode 2 includes the addition of the sealing layer 44. The sealing layer 44 protects parts of the interdigitated microelectrode 2 that are not required to be chemically active.

As an alternative to having electrical connection means 30, 36 in the form of through plated holes, electrical connections may be on edge or top surfaces of the interdigitated microelectrode 2. In this connection, it may be preferred to keep the top surface of the interdigitated microelectrode 2 free of any obstructions.

The gold ink employed is preferably ESL 8886A supplied by ESL Europe. The platinum ink employed is preferably ESL 5051 supplies by ESL Europe. The ceramic substrate is preferably Maruwa HA-96-2 with a glaze of GS-40. This is a glazed ceramic substrate, but an unglazed ceramic substrate may also be used.

The interdigitated microelectrode 2 is especially advantageous in the form of an electrochemical sensor for water quality measurements. For example chlorine in the water may be measured. Alternatively, monochloramine and dissolved oxygen may be measured, especially in drinking water.

The use of thick film printing techniques and materials enables the construction of the interdigitated microelectrode 2 to be produced more economically and cost effectively than known expensive microelectronic methods used in producing interdigitated microelectrodes.

When the interdigitated microelectrode 2 is used with the second metal being gold, then chlorine in water is able to be detected. In order to measure all of the chlorine molecules present, it is necessary to generate protons on the second electrode. In applications including the presence of other contaminants such for example as iron and manganese, and at the potentials required to produce protons (over 1.0 volts, depending upon the ambient pH and temperature), a gold electrode can become fouled by metal oxide deposits or oxidised, severely limiting the life of the interdigitated microelectrode 2. In this case, another more robust material in the form of the different material employed for the first layer 6 is able to be used to drive the reaction to produce the protons, thereby avoiding the problems that would occur if the interdigitated microelectrode 2 were to be produced with the first and the second metals both being gold.

It is to be appreciated that the embodiments of the invention described above with reference to the accompanying drawings have been given by way of example only and that modifications may be effected.

The invention claimed is:

1. A process for producing an interdigitated microelectrode, which process comprises providing a substrate, providing a first layer of a first metal on the substrate, and providing a second layer of a second metal on the substrate, and the process being such that the first layer comprises a plurality of line microelectrodes which are connected at a first end and are not connected at a second end, the second layer comprises a plurality of line microelectrodes which are connected at a first end and are not connected at a second end, the line microelectrodes of the first layer and the line microelectrodes of the second layer extend into each other but do not touch each other thereby to form an interdigitated microelectrode array, the first layer of the first metal is a thick film printed first layer, the second layer of the second metal is a thick film printed second layer, the line width of the line microelectrodes of the second layer is such that the line width has been reduced after deposition of the second layer on the substrate, the line width has been reduced by thin film photolithography and etching, the line width has been reduced to less than 25 microns wide, the first metal is different from the second metal, and the second metal is gold.

2. A process according to claim 1 and including providing registration means for use in ensuring that the line microelectrodes of the first layer and the line microelectrodes of the second layer do not touch each other.

3. A process according to claim 1 and including providing first electrical connection means for the first layer of the first metal.

4. A process according to claim 1 and including providing second electrical connection means for the second layer of the second metal.

5. A process according to claim 1 and including providing a sealing layer which seals parts of the interdigitated microelectrode but which does not seal the interdigitated microelectrode array.

6. A process according to claim 1 in which the first metal is platinum, and in which the substrate is a ceramic substrate.

* * * * *